(12) United States Patent
Kanjickal et al.

(10) Patent No.: US 11,883,311 B2
(45) Date of Patent: Jan. 30, 2024

(54) INFLATABLE BALLOON AND COVER

(71) Applicant: W. L. Gore & Associates, Inc., Newark, DE (US)

(72) Inventors: Deenu G Kanjickal, Flagstaff, AZ (US); James J. Nickerson, Flagstaff, AZ (US); Thomas G. Triebes, Flagstaff, AZ (US)

(73) Assignee: W. L. Gore & Associates, Inc.

( * ) Notice: Subject to any disclaimer, the term of this patent is extended or adjusted under 35 U.S.C. 154(b) by 22 days.

(21) Appl. No.: 17/552,172

(22) Filed: Dec. 15, 2021

(65) Prior Publication Data

US 2022/0104957 A1     Apr. 7, 2022

Related U.S. Application Data

(60) Division of application No. 17/068,145, filed on Oct. 12, 2020, now Pat. No. 11,229,540, which is a
(Continued)

(51) Int. Cl.
| | |
|---|---|
| *B29C 65/00* | (2006.01) |
| *A61F 2/958* | (2013.01) |
| *A61F 2/962* | (2013.01) |
| *A61M 25/10* | (2013.01) |
| *A61F 2/07* | (2013.01) |

(52) U.S. Cl.
CPC ............. *A61F 2/958* (2013.01); *A61F 2/07* (2013.01); *A61F 2/962* (2013.01); *A61M 25/10* (2013.01); *A61M 25/1002* (2013.01); *A61M 25/1029* (2013.01); *B29C 66/5221* (2013.01); *A61F 2002/9583* (2013.01); *A61F 2210/0076* (2013.01); *A61M 25/1038* (2013.01); *A61M 2025/1004* (2013.01);
(Continued)

(58) Field of Classification Search
None
See application file for complete search history.

(56) References Cited

U.S. PATENT DOCUMENTS

| | | | |
|---|---|---|---|
| 5,021,043 A | 6/1991 | Becker et al. | |
| 5,476,589 A | 12/1995 | Bacino | |
| | (Continued) | | |

FOREIGN PATENT DOCUMENTS

| | | |
|---|---|---|
| CN | 1034889 A | 8/1989 |
| CN | 102139126 A | 8/2011 |
| | (Continued) | |

OTHER PUBLICATIONS

International Preliminary Report on Patentability received for PCT Patent Application No. PCT/US2014/017637, dated Sep. 24, 2015, 10 pages.
(Continued)

*Primary Examiner* — Christopher T Schatz
(74) *Attorney, Agent, or Firm* — Faegre Drinker Biddle & Reath (57) ABSTRACT

The present disclosure describes implantable medical devices comprising covers, such as a balloon cover. Such devices can comprise a first layer of a porous polymeric material, such as ePTFE, surrounded by layers of a porous polymeric material having an imbibed elastomer, such as polyurethane. The cover can be used to assist in deployment of an expandable implant, such as a stent-graft, within the body of the patient.

10 Claims, 3 Drawing Sheets

Related U.S. Application Data continuation of application No. 15/678,685, filed on Aug. 16, 2017, now Pat. No. 10,806,617, which is a continuation of application No. 15/446,588, filed on Mar. 1, 2017, now Pat. No. 10,893,964, which is a division of application No. 14/185,450, filed on Feb. 20, 2014, now Pat. No. 9,770,352.

(60) Provisional application No. 61/785,809, filed on Mar. 14, 2013.

(52) U.S. Cl.
CPC ........... *A61M 2025/1075* (2013.01); *A61M 2025/1081* (2013.01); *A61M 2025/1088* (2013.01)

(56) References Cited

U.S. PATENT DOCUMENTS

| | | | |
|---|---|---|---|
| 5,512,051 | A | 4/1996 | Wang et al. |
| 5,868,776 | A | 2/1999 | Wright |
| 5,968,091 | A | 10/1999 | Pinchuk et al. |
| 9,770,352 | B2 | 9/2017 | Kanjickal et al. |
| 10,251,766 | B2 | 4/2019 | Chuter |
| 10,806,617 | B2 | 10/2020 | Kanjickal et al. |
| 2002/0099431 | A1 | 7/2002 | Armstrong et al. |
| 2003/0194520 | A1 | 10/2003 | Simhambhatla |
| 2004/0215331 | A1 | 10/2004 | Chew et al. |
| 2005/0055077 | A1 | 3/2005 | Marco et al. |
| 2006/0135962 | A1 | 6/2006 | Kick et al. |
| 2006/0178721 | A1 | 8/2006 | Durcan et al. |
| 2007/0073328 | A1 | 3/2007 | Kennedy, II |
| 2008/0009799 | A1 | 1/2008 | Lap |
| 2008/0097300 | A1 | 4/2008 | Eskaros et al. |
| 2008/0125710 | A1 | 5/2008 | Hobson et al. |
| 2008/0140173 | A1 | 6/2008 | Skaros et al. |
| 2008/0319388 | A1 | 12/2008 | Slattery et al. |
| 2009/0182413 | A1 | 7/2009 | Burkart |
| 2010/0036481 | A1 | 2/2010 | Dubrul et al. |
| 2010/0049123 | A1 | 2/2010 | Alpini et al. |
| 2010/0318029 | A1 | 12/2010 | Pepper et al. |
| 2012/0071912 | A1 | 3/2012 | Campbell et al. |
| 2012/0310210 | A1 | 12/2012 | Campbell et al. |
| 2017/0172776 | A1 | 6/2017 | Kanjickal et al. |
| 2017/0340465 | A1 | 11/2017 | Kanjickal et al. |
| 2021/0022898 | A1 | 1/2021 | Kanjickal et al. |
| 2021/0068997 | A1 | 3/2021 | Kanjickal et al. |

FOREIGN PATENT DOCUMENTS

| | | |
|---|---|---|
| JP | 2001-511022 A | 8/2001 |
| JP | 2010-500112 A | 1/2010 |
| JP | 2014-516259 A | 7/2014 |
| WO | 98/09670 A2 | 3/1998 |
| WO | 2004/000375 A1 | 12/2003 |
| WO | 2004/003475 A1 | 1/2004 |
| WO | 2005/084582 A1 | 9/2005 |
| WO | 2007/078304 A2 | 7/2007 |
| WO | 2008/021006 A2 | 2/2008 |
| WO | 2008/021019 A2 | 2/2008 |
| WO | 2009/066330 A1 | 5/2009 |
| WO | 2012/122023 A2 | 9/2012 |

OTHER PUBLICATIONS

International Search Report and Written Opinion for Application No. PCT/US2014/017637 dated Jul. 2, 2014 (8 pages).

INFLATABLE BALLOON AND COVER

CROSS-REFERENCE TO RELATED APPLICATION

This application is a divisional of U.S. application Ser. No. 17/068,145, filed Oct. 12, 2020, which is a continuation of U.S. application Ser. No. 15/678,685, filed Aug. 16, 2017, now U.S. Pat. No. 10,806,617, issued Oct. 20, 2020, which is a continuation application of U.S. application Ser. No. 15/446,588 filed on Mar. 1, 2017, now U.S. Pat. No. 10,893,964, issued Jan. 19, 2021, which is a divisional application of U.S. application Ser. No. 14/185,450 filed on Feb. 20, 2014, now U.S. Pat. No. 9,770,352, issued Sep. 26, 2017, which claims priority to U.S. Provisional Application No. 61/785,809, filed on Mar. 14, 2013, wherein the above-listed applications are hereby incorporated by reference in their entireties.

FIELD

The present disclosure relates generally to medical balloons and, more specifically, to pleated medical balloons and covers.

BACKGROUND

Inflatable balloons and covers are frequently used in interventional medical procedures. For example, inflatable balloons can be used for angioplasty applications, such as coronary or peripheral angioplasties, as well to assist in implantation of an expandable medical device, such as a stent or stent-graft. Inflatable balloons can be coaxially surrounded by covers to improve performance of the inflatable balloon or provide particular functional or clinical advantages.

Typically, inflatable balloons and covers are delivered through the vasculature or other body conduit or cavity to a treatment area of a patient by a balloon catheter. Further, the balloon catheter can comprise an expandable implant, such as a stent or stent-graft, which coaxially surrounds the inflatable balloon and cover. Inflation of the inflatable balloon can deploy the expandable implant in a treatment area of a patient by providing sufficient force to expand the expandable implant against the tissue of a desired treatment area of the patient. Inflatable balloons and covers having improved inflation characteristics, such as, for example, lower inflation pressure and providing more uniform deployment of expandable implants, can be beneficial.

SUMMARY

In various embodiments, a medical balloon in accordance with the present disclosure comprises an outer cover of a continuously wrapped sheet, the sheet comprising an innermost porous polymer layer and a composite layer comprising a porous polymer imbibed with an elastomeric component.

In other embodiments, an outer cover for a medical balloon in accordance with the present disclosure comprises at least one pleat aligned along at least a portion of a longitudinal axis.

In yet other embodiments, a catheter assembly in accordance with the present disclosure comprises a catheter tube, a balloon coupled to the catheter tube and comprising at least one pleat when in a collapsed configuration, and an outer cover coaxially surrounding the balloon comprising at least one pleat, wherein an inner surface of the outer cover substantially conforms to an outer surface of the balloon.

In various embodiments, a method for forming a cover in accordance with the present disclosure comprises imbibing a portion of a first surface of a porous polymeric sheet with an elastomer to form an imbibed zone and an non-imbibed zone, wrapping the porous polymeric sheet on a mandrel such that the non-imbibed zone contacts a second surface of the porous polymeric sheet to form a first polymeric layer, and wrapping the porous polymeric sheet on the mandrel such that the imbibed zone contacts the second surface to form at least one composite layer comprising a porous polymer imbibed with an elastomeric component.

Further, a method for forming a cover in accordance with the present disclosure can comprise the steps of thermally treating the first polymeric layer and the at least one composite layer comprising a porous polymer imbibed with an elastomeric component to form the cover, allowing the cover to cool, removing the cover from the mandrel, coaxially surrounding a balloon with the cover, inflating the balloon and the cover to a working pressure, and pleating the balloon and the cover while deflating the balloon and the cover.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

DETAILED DESCRIPTION

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

As used herein, "medical devices" can include, for example, stents, grafts, stent-grafts, filters, valves, occluders, markers, mapping devices, therapeutic agent delivery devices, prostheses, pumps, heart valves, heart valve frames or pre-stents, sensors, closure devices, embolic protection devices, anchors, cardiac or neurostimulation leads, gastrointestinal sleeves, and other endoluminal devices or endoprosthesis that are inserted in the vasculature or other body lumen or cavity of a patient.

The medical devices, inflatable members, balloons, support structures, coatings, and covers, described herein can be biocompatible. As used herein, "biocompatible" means suited for and meeting the purpose and requirements of a medical device, used for long- or short-term implants or for non-implantable applications. Long-term implants are generally defined as devices implanted for more than about 30 days. Short-term implants are generally defined as devices implanted for about 30 days or less.

The term "proximal" refers, throughout the specification and in the claims, to a location or a portion of an endoprosthesis that when inserted is closer to a physician or clinician and/or is closer to an entry site through which the endoprosthesis and delivery system are passed. Similarly, the term "proximally" refers to a direction towards such a location.

Further, throughout this specification and in the claims, the term "distal" refers to a location or a portion of an endoprosthesis that when inserted is farther from a physician or clinician and/or is farther from an entry site through which the endoprosthesis and delivery system are passed. Similarly, the term "distally" refers to a direction away from such a location.

With continuing regard to the terms proximal and distal, this disclosure should not be narrowly construed with respect to these terms. Rather, the devices and methods described herein may be altered and/or adjusted relative to the anatomy of a patient.

As used herein, "deployment" refers to the actuation or placement of a device at a treatment site, such as for example, positioning of a stent at a treatment site and its subsequent radial expansion by a medical balloon, or positioning a self-expanding stent covered with a sleeve at a treatment site and removal of the sleeve to allow the stent to expand into apposition with the surrounding tissues. Deployment processes can occur in stages, such as for example, a first stage comprising the release of a sleeve to a configuration suitable to constrain the expandable device only to an intermediate configuration, a second stage comprising the removal of the sleeve altogether from the device, and/or a third stage comprising further expansion of the device by a medical balloon.

Various embodiments of the present disclosure comprise a catheter assembly configured to deliver a balloon or a balloon with cover to a treatment area of the vasculature of a patient. In accordance with embodiments of the disclosure, the catheter assembly comprises an inflatable balloon and cover. The inflatable balloon and cover can assist in deployment of an expandable implant such as, for example, a stent-graft, by providing pressure against the inner surface of the expandable implant, which can fully expand the implant and engage it with the walls of the vasculature. Benefits of catheter assemblies in accordance with the present disclosure may include improved deployment characteristics of the balloon, cover, and/or expandable implant by improving the operating characteristics of the balloon and/or cover, such as decreasing the inflation pressure and improving the uniformity of the inflation of the balloon or balloon with cover.

Figure 1:
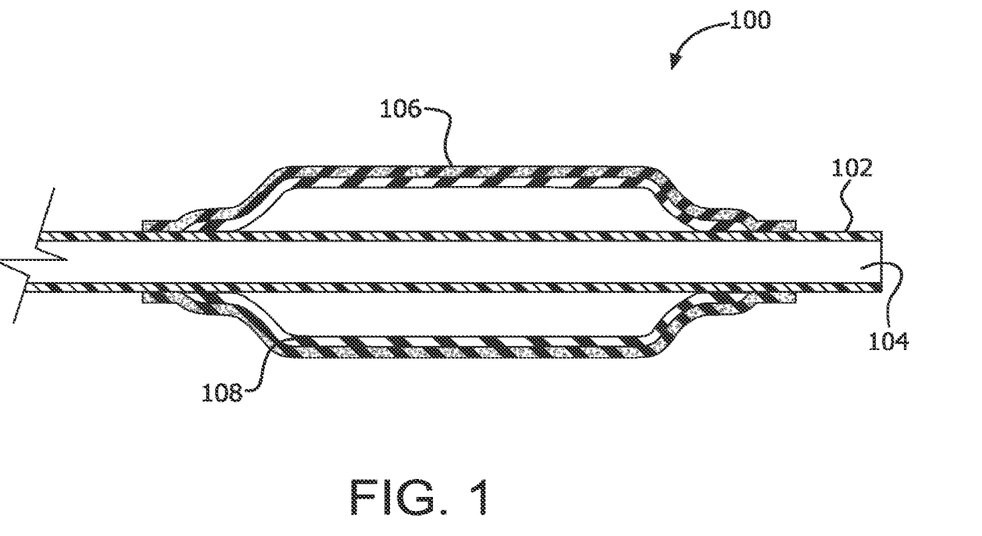
FIG. 1 illustrates a side view of a medical device in accordance with the present disclosure.

With initial reference to FIG. 1, a catheter assembly 100 in accordance with the present disclosure is illustrated. Catheter assembly 100 comprises a catheter tube 102 with a continuous lumen 104. A cover 106 that coaxially surrounds balloon 108 is coupled to catheter tube 102 and continuous lumen 104 at or near the distal end of catheter tube 102. Attachment of cover 106 to catheter tube 102 can be accomplished in various ways, including adhering the proximal and distal ends of cover 106 to catheter tube using an adhesive, such as, for example, a cyanoacrylate adhesive.

In various embodiments, balloon 108 comprises a generally tubular shaped balloon capable of inflating within the vasculature of a patient upon pressurization. For example, a biocompatible fluid, such as, for example, water or saline, can be introduced into catheter tube 102, pass through continuous lumen 104 and through an inflation port (not shown) in catheter tube 102 located at the interior of balloon 108, and pressurize balloon 108. As pressure to balloon 108 is increased, the diameter of balloon 108 is also increased.

Balloon 108 can comprise, for example, a non-compliant, generally inelastic balloon. In such embodiments, balloon 108 can comprise a material that is configured to allow balloon 108 to expand to a chosen diameter upon sufficient pressurization and remain at or near the set diameter under further pressurization until a burst pressure is reached, such as, for example, nylon, polyethylene, polyethylene terephthalate (PET), polycaprolactam, polyesters, polyethers, polyamides, polyurethanes, polyimides, ABS copolymers, polyester/poly-ether block copolymers, ionomer resins, liquid crystal polymers and rigid rod polymers.

In various embodiments, balloon 108 can comprise a compliant, relatively elastic balloon. In such embodiments, balloon 108 can comprise a material that is configured to allow balloon 108 to continuously increase in diameter as pressure to balloon 108 is increased, such as, for example polyurethanes, latex and elastomeric organosilicone polymers, such as, polysiloxanes. When a distension limit is reached, balloon 108 can rupture.

In yet other embodiments, balloon 108 comprises a semi-compliant balloon. In such embodiments, balloon 108 behaves in a combination of compliant and semi-compliant attributes. Although described in connection with compliant and non-compliant embodiments, any material or configuration that allows balloon 108 to inflate in a predictable manner within the body of a patient, including in a combination of compliant and non-compliant behavior, is within the scope of the present disclosure.

Figure 2:
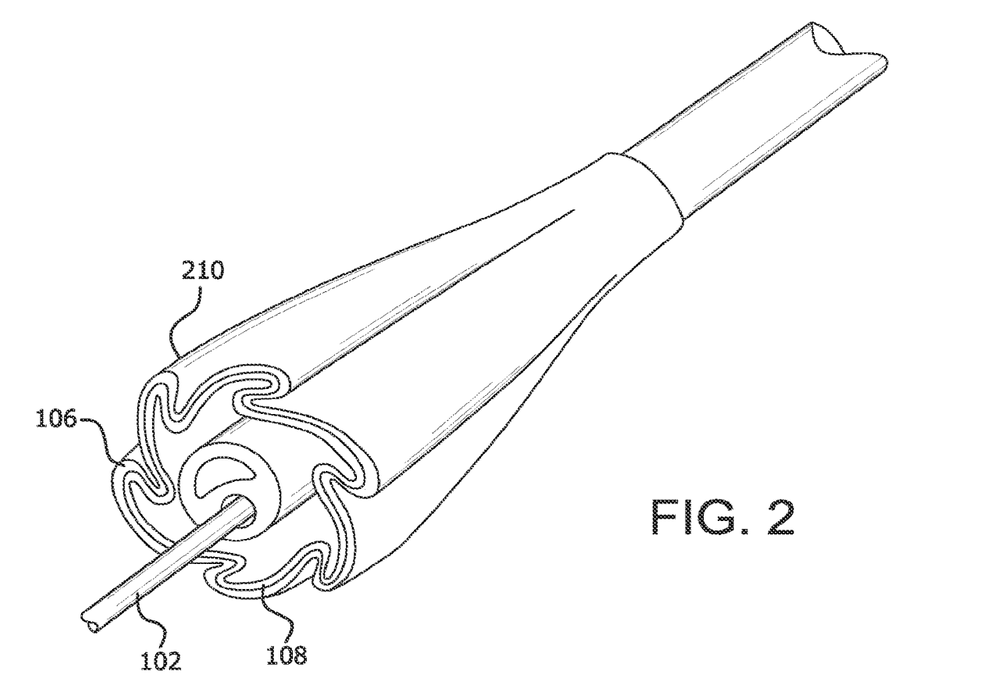
FIG. 2 illustrates a perspective view of a medical device in accordance with the present disclosure.

With reference to FIG. 2, in various embodiments, balloon 108 can comprise a plurality of pleats 210. Pleats 210 can comprise, for example, folds or inflection points in the material of balloon 108 extending generally along at least a portion of the longitudinal axis of balloon 108. In such embodiments, balloon 108 comprises a generally tubular shape having one or more pleats 210.

In various embodiments, balloon 108 can be coaxially surrounded by cover 106. Cover 106 can comprise an inner surface that can substantially conform to an outer surface of balloon 108, such that both balloon 108 and cover 106 comprise substantially the same shape, including when balloon 108 is deflated. However, in other embodiments, cover 106 can comprise a different shape or configuration from balloon 108.

In various embodiments, cover 106 can comprise a plurality of pleats 210. Similarly to balloon 108, pleats 210 can comprise, for example, folds or inflection points in the material of cover 106 extending generally along at least a portion of the longitudinal axis. In such embodiments, cover 106 comprises a generally tubular shape having two or more pleats 210. In various embodiments, cover 106 comprises the same number of pleats 210 as balloon 108. In various embodiments, along at least a section of or the entire working length of balloon cover 106, the inner surface of balloon cover 106 interfaces with the outer surface of balloon 108 in both the pleated, collapsed configuration and the un-pleated, inflated configuration.

Pleats 210 can be formed in cover 106 and balloon 108 simultaneously. For example, balloon 108 can be coaxially surrounded by cover 106, and pleats 210 can then be formed in both balloon 108 and cover 106.

In other embodiments, pleats 210 can be formed in cover 106 after pleats 210 are formed in balloon 108. For example, a pre-pleated balloon 108 can be coaxially surrounded by cover 106. In such embodiments, both cover 106 and pre-pleated balloon 108 can be inflated together to a working pressure, after which cover 106 and balloon 108 are subjected to a mechanical pleat forming process that can form, for example, the same number and configuration of pleats in cover 106 as in pre-pleated balloon 108. While forming pleats 210 in cover 106, both cover 106 and balloon 108 can be deflated and compacted for delivery into the body of a patient. Although described in specific embodiments, any manner of forming pleats in cover 106 is within the scope of the present disclosure.

In yet other embodiments, balloon 108 can comprise a plurality of pleats 210 and cover 106 can comprise no pleats 210. In such embodiments, pleats 210 can be formed in balloon 108, followed by cover 106 being placed coaxially around the outer surface of balloon 108. Although described in connection with specific examples (i.e., balloon 108 and cover 106 both comprising pleats or only balloon 108 comprising pleats), any configuration in which balloon 108 and/or cover 106 comprises a plurality of pleats is within the scope of the present disclosure.

Cover 106 can comprise, for example, a polymer such as, for example, expanded fluoropolymers, such as, expanded polytetrafluoroethylene (ePTFE), modified (e.g., densified) ePTFE, and expanded copolymers of PTFE. In various embodiments, the expanded fluoropolymer can comprise a node and fibril microstructure. In various embodiments, the expanded fluoropolymer can be highly fibrillated (i.e., a non-woven web of fused fibrils. Although described in connection with specific polymers, any material or configuration that allows cover 106 to inflate in a predictable manner within the body of a patient is within the scope of the present disclosure.

In various embodiments, cover 106 can comprise multiple layers of a polymeric material. For example, cover 106 can comprise a polymeric material continuously wrapped over a substrate or mandrel to form a generally tubular member. In various embodiments, cover 106 can be constructed with circumferential-, helical-, or axial-orientations of the polymeric material. "Orientations," as used herein, the directional orientation of a property of the polymeric material, e.g., orientations of the strength of the material and/or the microstructure of the material. In such embodiments, the polymeric material can be wrapped generally perpendicular to the longitudinal axis of the mandrel or substrate, i.e., circumferentially wrapped. In other embodiments, the material can be wrapped at an angle between greater than 0 degrees and less than 90 degrees relative to the longitudinal axis of the mandrel or substrate, i.e., helically wrapped. In yet other embodiments, the polymeric material can be wrapped generally parallel to the longitudinal axis of the mandrel or substrate, i.e., axially (or longitudinally) wrapped.

In various embodiments, cover 106 can comprise an inner surface that is a low friction surface to facilitate unfolding of the pleats on cover 106 and/or balloon 108 during inflation. For example, the inner surface of cover 106 can comprise or consist essentially of ePTFE. Alternatively or in addition thereto, a lubricious agent can be applied to the inner surface of cover 106. Further, in various embodiments, cover 106 can comprise an outer surface that is a low friction surface to facilitate deployment of a medical device. For example, the outer surface of cover 106 can comprise or consist essentially of ePTFE. Alternatively or in addition thereto, a lubricious agent can be applied to the outer surface of cover 106, such as a dry lubricious coating.

In other embodiments, cover 106 can comprise an inner surface that is a high friction surface or adhesive coating to facilitate attachment of cover 106 to balloon 108. For example, at least a portion of cover 106 can comprise a coating, such as fluorinated ethylene propylene, that can assist in attachment of the inner surface of cover 106 to the outer surface of balloon 108.

Cover 106 can comprise, for example, a non-porous polymer. In such embodiments, the non-porous polymer can reduce and/or eliminate leaking of inflation fluid through cover 106 and into the body of the patient. Further, the non-porous polymer can reduce and/or eliminate blood entering cover 106 and/or balloon 108.

In various embodiments, cover 106 can also comprise a coating that provides a therapeutic benefit to the patient. For example, cover 106 can comprise a coating such as heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others. Any coating that can assist in deployment of cover 106 and/or balloon 108 is within the scope of the present disclosure.

Figure 3:
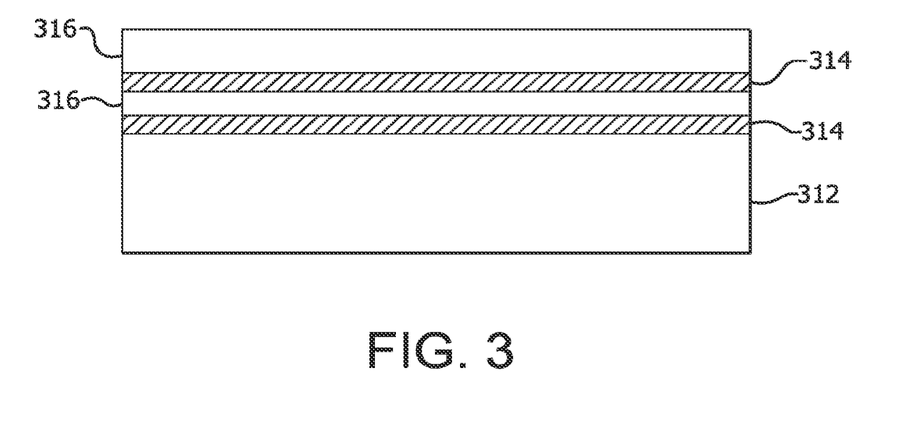
FIG. 3 illustrates a cross sectional view of a medical device in accordance with the present disclosure.

Cover 106 can comprise, for example, a porous polymeric material the surface of which is at least partially imbibed with an elastomer. In various embodiments, cover 106 can comprise multiple layers of porous polymer imbibed with an elastomer. With reference to FIG. 3, cover 106 can comprise an innermost porous polymer layer 312 and at least one composite layer 316. In such embodiments, composite layer 316 can comprise a porous polymer imbibed with an elastomer 314. As illustrated in FIG. 3, multiple composite layers 316 can coaxially surround innermost porous polymer layer 312. In various embodiments, the outermost layer of cover 106 is a composite layer 316, and the outer surface of cover 106 is substantially free of elastomer.

In various embodiments, innermost porous polymer layer 312 can comprise a layer of porous polymer that has a greater thickness than at least one composite layer 316. For example, innermost porous polymer layer 312 can comprise a layer of at least twice the thickness of one or more composite layers 316.

Innermost porous polymer layer 312 and/or composite layers 316 can comprise, for example, expanded polytetrafluoroethylene (ePTFE), ultra-high molecular weight polyethylene. However, any porous polymer that is biocompatible and capable of being imbibed with a suitable elastomer is within the scope of the present disclosure.

Elastomer 314 can comprise, for example, a polyurethane (e.g., Tecothane®). However, any suitable elastomer is within the scope of the present disclosure.

Figure 4:
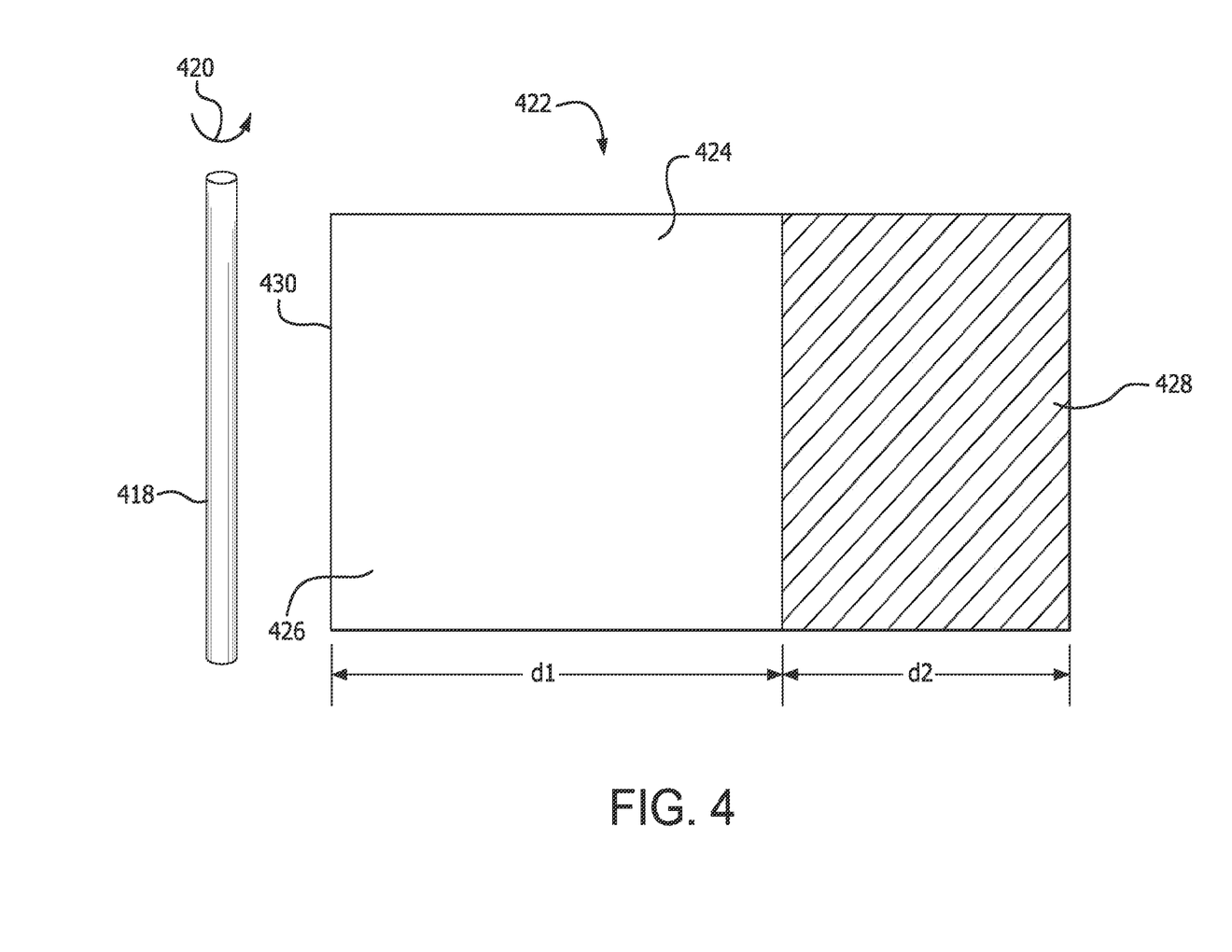
FIG. 4 illustrates a material used to create a medical device in accordance with the present disclosure.

In various embodiments, cover 106 can comprise layers of porous polymer and elastomer formed by a zone imbibing and wrapping process. For example, as illustrated in FIG. 4, a sheet 422 having a first surface 424 and a second surface 430 can comprise a porous polymeric material, such as ePTFE.

In various embodiments, sheet 422 can comprise an imbibed zone 428 and a non-imbibed zone 426. Imbibed zone 428 can be formed, for example, by imbibing sheet 422 with an elastomer, such as elastomer 314, in a portion of first surface 424 of sheet 422. Imbibed zone 428 can be formed by, for example, "butter coating" or slot die coating. In such embodiments, an elastomeric material such as elastomer 314 is imbibed into a surface of sheet 422 throughout imbibed zone 428. In various embodiments, the elastomer imbibed into first surface 424 can comprise a polyurethane.

After imbibed zone 428 is prepared, sheet 422 can be formed into a generally tubular member. In various embodiments, sheet 422 can be wrapped around a mandrel 418 to form a generally tubular member. For example, the porous polymer of sheet 422 can comprise an anisotropic polymer, such that sheet 422 possesses a higher matrix tensile strength in a particular direction. In such configurations, sheet 422 can be oriented relative to mandrel 418 such that sheet 422 is wrapped around mandrel 418 in a direction 420 of wrapping that is substantially perpendicular to the direction of higher matrix tensile strength; i.e., the higher matrix tensile strength is oriented axially. In other configurations, sheet 422 can be oriented relative to mandrel 418 and wrapped around mandrel 418 whereby the higher matrix tensile strength of sheet 422 is helically oriented. In yet other configurations, sheet 422 can be oriented relative to mandrel 418 and wrapped around mandrel 418 whereby the higher matrix tensile strength of sheet 422 is circumferentially oriented.

In other embodiments, sheet 422 comprises an isotropic porous polymer. In such embodiments, sheet 422 can be wrapped around mandrel 418 in a direction 420 that is not related to a direction of higher or lower matrix tensile strength.

In various embodiments, and with reference to FIGS. 3 and 4, the dimensions of non-imbibed zone 426 can correspond with a desired thickness of innermost porous polymer layer 312. For example, non-imbibed zone 426 can comprise a depth d1, which can correspond with direction 420. In various embodiments, depth d1 corresponds with the desired thickness of the innermost porous polymer layer 312. For example, mandrel 418 can comprise a perimeter, and depth d1 can be equal or greater than the perimeter. In such configurations, sheet 422 can be wrapped around mandrel 418 such that the non-imbibed zone 426 of first surface 424 contacts second surface 430 to form innermost porous polymer layer 312 with the thickness of sheet 422. In other embodiments, depth d1 be equal to or greater than twice the perimeter of mandrel 418, such that innermost porous polymer layer 312 has a thickness at least twice that of non-imbibed zone 426 of sheet 422.

In various embodiments, imbibed zone 428 of first surface 424 comprises a depth d2. In such embodiments, depth d2 can correspond with the desired number of composite layers 316. For example, depth d2 can be equal to or greater than a perimeter of mandrel 418, which can result in a single composite layer 316. In other embodiments, depth d2 can be equal to or greater than twice the perimeter of mandrel 418, which can result in two or more composite layers 316.

In various embodiments, balloon 108 and cover 106 can be thermally bonded to one another. In such embodiments, at least a portion of balloon 108 and cover 106 can be bonded to each other. Such thermal bonding can be temporary, and can facilitate uniform deployment of balloon 108 and cover 106. Any manner of bonding, including non-thermal techniques, that provides for uniform deployment of balloon 108 and cover 106 is within the scope of the present disclosure.

Figure 5:
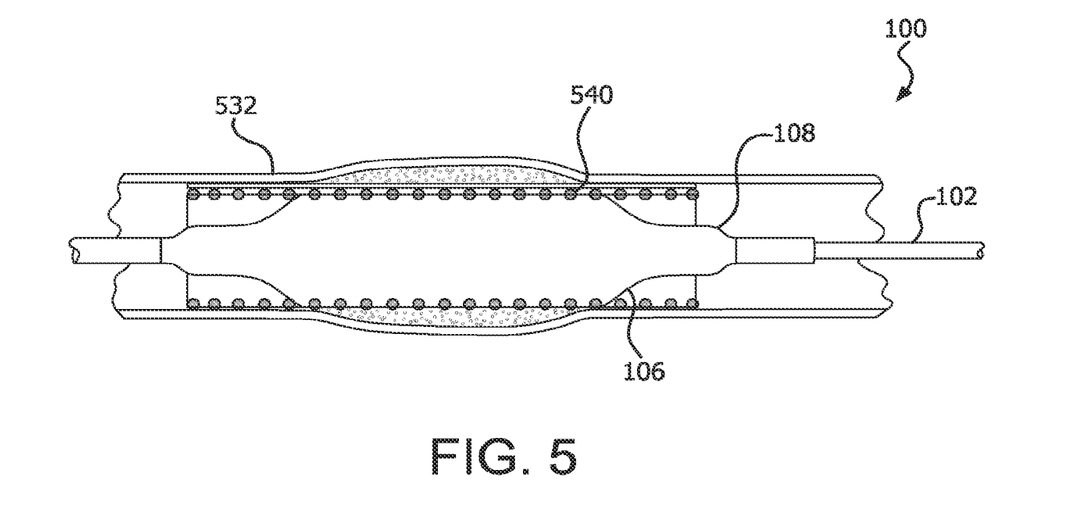
FIG. 5 illustrates a side view of a medical device in accordance with the present disclosure.

With reference to FIG. 5, in various embodiments, catheter assembly 100 further comprises an expandable implant 540. In such embodiments, expandable implant 540 can be positioned coaxially around balloon 108 and/or cover 106, such that inflation of balloon 108 and/or cover 106 can cause expansion of expandable implant 540.

Expandable implant 540 can comprise, for example, a balloon expandable implant. In such configurations, inflation of balloon 108 and/or cover 106 is required to cause expansion of expandable implant 540. Sufficient inflation of balloon 108 and/or cover 106 can cause deployment of expandable implant 540 by, for example, causing all or a portion of expandable implant 540 to expand against a vessel wall 532. In various embodiments, after deployment of expandable implant 540, balloon 108 and cover 106 can be deflated, and catheter assembly 100 can be removed from the body of the patient.

In other embodiments, expandable implant 540 can comprise a self-expanding implant. Such devices dilate from a radially collapsed configuration to a radially expanded configuration when unconstrained. In such configurations, expandable implant 540 can be partially deployed within the vasculature of a patient by removing any member constraining expandable implant, allowing it to expand to a radially expanded configuration, including a partially deployed configuration. In various embodiments, balloon 108 and/or cover 106 can be inflated to cause partially deployed expandable implant 540 to expand to a fully deployed configuration. For example, expandable implant 540 can be expanded by balloon 108 and/or cover 106 such that all or part of expandable implant 540 contacts vessel wall 532.

In various embodiments, expandable implant 540 comprises at least one stent member and optionally a graft member. In various embodiments, the at least one stent member comprises a biocompatible material. For example, stent members can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; malleable and non-malleable metals, including stainless steels, cobalt-chromium alloys and nitinol, and biologically derived materials such as bovine arteries/veins, pericardium and collagen. Stent members can also comprise bioresorbable materials such as poly(amino acids), poly(anhydrides), poly(caprolactones), poly(lactic/glycolic acid) polymers, poly(hydroxybutyrates) and poly (orthoesters), and biodegradable metals and metal alloys. Any material that is biocompatible and provides adequate support to the vasculature of a patient is in accordance with the present disclosure.

Stent members can comprise, for example, various configurations such as rings, joined rings, cut tubes, wound wires (or ribbons), or flat patterned sheets rolled into a tubular form. However, any configuration of stent members that can be implanted in and provide support to the vasculature of a patient is in accordance with the present disclosure.

In various embodiments, the stent member can comprise one or more anchors. For example, one or more anchors can be located at or near one or both ends of the stent member. In such configurations, anchors can engage and attach to the vasculature of the patient to maintain expandable implant 540 in a desired position within the vasculature. In various embodiments, balloon 108 and/or cover 106 can be inflated to cause the anchors to engage in vessel wall 532, which can assist in maintaining expandable implant 540 in the desired position. The use of any number and configuration of anchors is within the scope of the present disclosure.

In various embodiments, expandable implant 540 comprises a graft member. Graft members can comprise a biocompatible material that provides a lumen for blood flow within a vasculature, such as, for example ePTFE. Any graft member that provides a sufficient lumen for blood flow within a vasculature is in accordance with the present disclosure.

Example 1

An ePTFE membrane was obtained which was made generally in accordance with the teachings of U.S. Pat. No. 5,476,589 issued to Bacino, which is incorporated herein by reference in its entirety for all purposes. The membrane was slit to approximately 90 mm in width and rolled with the machine direction extending parallel to the roll length. A portion of the membrane, approximately 65% of the roll width (about 60 mm) was imbibed with polyurethane (Tecothane® 1074 (Lubrizol Corporation, Wickliffe, Ohio, USA) in accordance with the general teachings of US Patent Application Publication No. 2008/0125710 to Hobson, et al., which is incorporated herein by reference.

The polyurethane in the imbibed portion extended only part way through the underlying ePTFE membrane and a coating was created on the surface. The imbibed portion had a thickness of about 10 microns. The remaining approximately 35% of the roll width (about 30 mm) was left unimbibed (the "tail").

The ePTFE on the unimbibed portion had the following properties: thickness=0.00635 mm, density=0.42 g/cc, matrix tensile strength in the strongest (machine) direction=18049 psi, matrix tensile strength in the transverse direction (orthogonal to the strongest direction)=458 psi.

A sheet of regionally imbibed ePTFE was cut from the roll, wherein the sheet had a length of 150 mm. A mandrel having a diameter of 2.2 mm, length of 220 mm, and comprising stainless steel was selected. The tail of the sheet was placed on top of the imbibed portion. The sheet was continuously wrapped around the mandrel by orienting the strongest direction of the sheet parallel to the axis of the mandrel. The unimbibed tail was wrapped around the mandrel first, and the wrapping continued to wrap the remainder of the sheet onto the mandrel with the polyurethane coating facing in the direction of the mandrel. The sheet was wrapped around the mandrel a total of approximately 13⅓ times.

The wrapped mandrel was thermally treated at 230° C. for approximately 3 minutes, and then allowed to cool to room temperature. The ends of the wrapped sheet where then trimmed to a length slightly longer than the balloon to which the cover was to be applied. The balloon selected was a nylon balloon mounted on a catheter (model number 08GK-762C, manufactured by Bavaria Medizin Technologie (BMT), D-82234 Oberpfaffenhofen, Germany).

The wrapped sheet, now in the form of a tubular member, was removed from the mandrel and positioned coaxially around the balloon. The cover and balloon were compressed in a die to remove air between the two components. A thin layer of Dymax® adhesive (Model Number 204-CTH, Dymax Corp., Torrington, CT, USA) was applied to each end of the cover and adjacent catheter shaft, and the adhesive was cured. Four layers of ePTFE tape were wrapped around each end of the cover and catheter shaft, and additional adhesive was applied and cured.

The cover and balloon were inflated to about 6 atmospheres and inspected for leaks or defects. After deflation, the cover and balloon were placed into a pleating die. The cover and balloon were inflated to about 2 atmospheres, and then the pleating die was applied concurrently with a vacuum of about −0.5 atmospheres. The cover and balloon were then placed into a compression die that rolled the pleats in a radial direction.

A stent graft comprising stainless steel stent rings and ePTFE luminal and adluminal covers was positioned coaxially over the cover and balloon and lightly crimped. The cover, balloon, and stent were then compressed to a desired profile for delivery into the body of the patient.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A method of making a medical balloon assembly, the method comprising:
   coaxially receiving a cover having an inner surface and an outer surface over a balloon having a length and an outer surface; and
   temporarily bonding at least a portion of the inner surface of the outer cover to the outer surface of the balloon, the outer cover having an outer layer including a polymer membrane and an elastomer component imbibed in the polymer membrane and an inner layer that is non-imbibed with the elastomer component.

2. The method of claim 1, wherein temporarily bonding at least a portion of the inner surface of the outer cover to the outer surface of the balloon includes thermally bonding the portion of the inner surface of the outer cover to the outer surface of the balloon.

3. The method of claim 1, wherein the inner surface of the cover is a low friction surface.

4. The method of claim 1, further comprising providing the inner surface of the outer cover with a lubricious agent.

5. The method of claim 1, further comprising providing the outer surface of the outer cover with a lubricious agent.

6. The method of claim 1, wherein the inner surface of the outer cover is a high friction surface.

7. The method of claim 1, further comprising providing the inner surface of the outer cover with an adhesive coating defining a high friction surface.

8. The method of claim 7, wherein the adhesive coating comprises fluorinated ethylene propylene.

9. The method of claim 1, further comprising imbibing the elastomer component in the polymer membrane.

10. The method of claim 1, wherein the outer surface of the outer cover is substantially free of elastomer.

* * * * *